US005501951A

United States Patent [19]

Milliman

[11] Patent Number: 5,501,951

[45] Date of Patent: Mar. 26, 1996

[54] NUCLEIC ACID PROBES TO COCCIDIOIDES IMMITIS

[75] Inventor: Curt L. Milliman, St. Louis, Mo.

[73] Assignee: Gen-Probe Incorporated, San Diego, Calif.

[21] Appl. No.: 178,014

[22] Filed: Jan. 6, 1994

Related U.S. Application Data

[63] Continuation of Ser. No. 811,052, Dec. 18, 1991, Pat. No. 5,284,747.

[51] Int. Cl.$^6$ .............................. C07H 21/04; C12Q 1/68

[52] U.S. Cl. .......................... 435/6; 536/24.3; 536/24.32; 536/24.33

[58] Field of Search ............................... 435/6; 536/24.3, 536/24.32, 24.33

[56] References Cited

U.S. PATENT DOCUMENTS

| | | |
|---|---|---|
| 4,689,295 | 8/1987 | Taber et al. . |
| 5,030,557 | 8/1991 | Hogan et al. . |
| 5,284,747 | 2/1994 | Milliman .................................... 435/6 |

FOREIGN PATENT DOCUMENTS

| | | |
|---|---|---|
| 3138784 | 8/1984 | Australia . |
| 0133671 | 3/1985 | European Pat. Off. . |
| 0155359 | 9/1985 | European Pat. Off. . |
| 0232085 | 8/1987 | European Pat. Off. . |
| 0245129 | 11/1987 | European Pat. Off. . |
| 0250662 | 1/1988 | European Pat. Off. . |
| 0277237 | 8/1988 | European Pat. Off. . |
| 8301073 | 3/1983 | WIPO . |
| 8402721 | 7/1984 | WIPO . |
| 8803957 | 6/1988 | WIPO . |

OTHER PUBLICATIONS

Baess, "Deoxyribonucleic Acid Relationships Between Different Serovars of *Mycobacterium avium, Mycobacterium intracellulare* and *Mycobacterium scrofulaceum,*" *Adv. Path. Microbiol. Immunol. Scand. Sect. B* 91:201–203 (1983).

Baess, "Deoxyribunucleic Acid Relatedness Among Species of Rapidly Growing Mycobacteria," *Acta. Path. Microbiol. Immunol. Scand. Sect. B.* 90:371–375 (1982).

Baess and Bentzon, "Deoxyribonucleic Acid Hybridization Between Different Species of Mycobacteria," *Adv. Path. Microbiol. Scand. Sect. B.* 86:71–76 (1978).

*Bergy's Manual of Systematic Bacteriology* 1:160 (1984).

*Bergy's Manual of Systematic Bacteriology,* p. 283 (1984).

Boddinghaus et al., "Detection and Identification of Mycobacteria by Amplification of rRNA," *Journal of Clinical Microbiology* 28:1751–1759 (1990).

Bradley, "Relationships Among Mycobacteria and Nocardiae Based upon Deoxyribonucleic Acid Reassociation," *Journal of Bacteriology* 113:645–651 (1973).

Brenner, "Deoxyribonucleic Acid Reassociation in the Taxonomy of Enteric Bacteria," *International Journal of Systematic Bacteriology,* 23:298–307 (1973).

Brenner, "Facultatively Anaerobic Gram–Negative Rods," from *Bergy's Manual of Systematic Bacteriology* 1:408–410 (1984).

Brenner et al., "Ten New Species of *Legionella,*" *International Journal of Systematic Bacteriology* 35:50–59 (1985).

Brenner et al., "DNA percent relatedness among Legionellae —Table 4—from Family *Legionellaceae,*" *International Journal Systematic Bacteriology* 30:236 (1980).

Brenner et al., "Classification of the Legionnaires' Disease Bacterium: An Interim Report," *Current Microbiology* 1:71–75 (1978).

Brenner et al., "Classification of the Legionnaires' Disease Bacterium: *Legionella pneumophila,* genus novum, species nova, of the Family Legionellaceae, familia nova," *Annals of Internal Medicine* 90:656–658 (1979).

Brosius et al., "Complete nucleotide sequence of a 23S ribosomal RNA gene from *Excherichia coli,* " *Proc. Natl. Acad. Sci. USA* 77:201–204 (1980).

Brosius et al., "Complete nucleotide sequence of a 16S ribosomal RNA gene from *Excherichia coli,*" *Proc. Natl. Acad. Sci. USA* 75:4801–4805 (1978).

Carbon et al., "The sequence of the ribosomall 16S RNA from *Protcus vulgaris,*" *Nucleic Acids Research* 9:2325–2333 (1981).

Colwell et al., "Numerical Taxonomy and Deoxyribonucleic Acid Reassociation in the Taxonomy of Some Gram–Negative Fermentative Bacteria," *International Journal of Systematic Bacteriology* 24:422–433 (1974).

Crosa et al., "Polynucleotide Sequence Divergence in the Genus Citrobacter," *Journal of General Microbiology* 83:271–282 (1974).

Festl et al., "DNA hybridization Probe for the *Pseudomonas fluorescens Group,*" *Applied and Environmental Microbiology* 52:1190–1194 (1986).

Göbel and Stanbridge, "Cloned Mycoplasma Ribosomal RNA Genes for the Detection of Mycoplasma Contamination in Tissue Cultures," *Science* 226:1211–1213 (1984).

Göbel et al., "Oligonucleotide Probes Complementary to Variable Regions of Ribosomal RNA Discriminate between *Mycoplasma* Species," *Journal of General Microbiology* 133:1969–1974 (1987).

Goodfellow and Wayne, in *The Biology of the Mycobacteria* Ralledge & Stanford eds. (Acad. Press:1982) vol. 1, pp. 476–479.

Grimont et al., "DNA Probe Specific for *Legionella pneumophila,*" *J. Clin. Microbiol.* 21:431–437 (1985).

(List continued on next page.)

*Primary Examiner*—W. Gary Jones
*Assistant Examiner*—Paul B. Tran
*Attorney, Agent, or Firm*—Lyon & Lyon

[57] ABSTRACT

The present invention concerns oligonucleotide probes for detecting *Coccidioides immitis.* The probes are capable of distinguishing between *Coccidioides immitis* and closely related phylogenetic neighbors. These probes are targeted to unique *Coccidioides immitis* 28S rRNA and gene sequences encoding 28S rRNA, and may be used in an assay for the detection and/or quantitation of *Coccidioides immitis,* e.g., in samples of sputum, urine, blood, tissue sections, food, soil and water.

16 Claims, No Drawings

OTHER PUBLICATIONS

Kilpper–Bälz and Schleifer, "DNA–rRNA Hybridization Studies Among Staphylococci And Some Other Gram–Positive Bacteria," *FEMS Microbiology Letters* 10:357–362 (1981).

Kilpper–Bälz et al., "Nucleic Acid Hybridization of Group N and Group D Streptococci," *Current Microbiology* 7:245–250 (1982).

Kohne, "Application of DNA probe tests to the diagnosis of infectious disease," *American Clinical Products Review,* Nov. (1986).

Kohne et al., "Nucleic Acid Probe Specific for Members of the Genus Legionella," in *Proceedings of the Second International Symposium, American Society for Microbiology,* C. Thornsbury, A. Balows, J. C. Freeley, and W. Jakukowski eds. (Washington D.C.) pp. 107–108.

Lane et al., "Rapid determination of 16S ribosomal RNA sequences for phylogenetic analyses," *Proc. Natl. Acad. Sci. USA* 82:6955–6959 (1985).

Lau et al., "Phylogenetic Diversity and Position of the Genus Campylobacter," *System Appl. Microbiol.* 447:1–13 (1987).

Ludwig and Stackebrandt, "A phylogenetic analysis of Legionella," *Archives of Microbiology* 135:45–50 (1983).

Malouin et al., "DNA Probe Technology for Rapid Detection of *Haemophilus influenzae* in Clinical Specimens," *J. Clin. Microbiol.* 26:2132–2138 (1988).

McCarroll et al., "Nucleotide Sequence of the *Dictyostelium discoideum* Small–Subunit Ribosomal Ribonucleic Acid Inferred from the Gene Sequence: Evolutionary Implications," *Biochemistry* 22:5858–5868 (1983).

Mordarski et al., "Ribosomal Ribonucleic Acid Similarities in the Classification of Rhodococcus and Related Taxa," *Journal of General Microbiology* 118:313–319 (1980).

Razin, *Microbiol. Rev.* 49:437 (1985).

Razin, "Molecular Biology and Genetics of Mycoplasmas (*Mollicutes*)," *Microbiological Reviews* 49:419–455 (1985).

Razin et al., "Molecular and Biological Features of Mollicutes (Mycoplasmas)," *Ann. Microbiol.* 135:9–15 (1984).Rogers et al., "Construction of the mycoplasma evolutionary tree from 5S rRNA sequence data," *Proc. Natl. Acad. Sci. USA* 82:1160–1164 (1985).

Saxe and Kimmel, *Molecular and Cellular Biology* 10:2367–2378 (1990).

Schleifer and Kilpper–Bälz, "Transfer of *Streptococcus faecalis* and *Streptococcus faecium* to the Genus *Enterococcus nom.* rev. as *Enterococcus faecalis* comb. nov. and *Enterococcus faecium* comb. nov.," *International Journal of Systematic Bacteriology* 34:31–34 (1984).

Stackebrandt and Schleifer, "Molecular Systematics of Actinomycetes and Related Organisms," *Biological, Biochemical, and Biomedical aspects of Actinomycetes* p. 485 (1984).

Stahl, "Evolution, Ecology, and Diagnosis: Unity in Variety," *Biotechnology* 4:623– 628 (1986).

Veldman et al., "The primary and secondary structure of yeast 26S rRNA," *Nucleic Acids Research* 9:6935–6953 (1981).

Weisburg et al., "Eubacterial origin of *Chlamydiae,*" *Journal of Bacteriology* 167:570–574 (1986).

Yogev and Razin, "Common Deoxyribonucleic Acid Sequences in *Mycoplasma genitalium and Mycoplasma pneumoniae* Genomes," *International Journal of Systematic Bacteriology* 36:426–430 (1986).

NUCLEIC ACID PROBES TO COCCIDIOIDES IMMITIS

This is a continuation of application Ser. No. 07/811,052, filed Dec. 18, 1991, now U.S. Pat. No. 5,284,747.

FIELD OF THE INVENTION

This invention relates to detection of *Coccidioides immitis* in a sample, and to use of nucleic acid probes for specific detection of a desired organism.

BACKGROUND OF THE INVENTION

Two single strands of deoxyribo- ("DNA") or ribo- ("RNA") nucleic acid, formed from nucleotides (including the bases adenine (A), cytosine (C), thymidine (T), guanine (G), uracil (U), or inosine (I)), may associate ("hybridize") to form a double stranded structure in which the two strands are held together by hydrogen bonds between pairs of complementary bases. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs.

When a first single strand of nucleic acid contains sufficient contiguous complementary bases to a second, and those two strands are brought together under conditions which will promote their hybridization, double stranded nucleic acid will result. Under appropriate conditions, DNA/DNA, RNA/DNA, or RNA/RNA hybrids may be formed.

A probe is generally a single stranded nucleic acid sequence which is complementary to some degree to a nucleic acid sequence sought to be detected ("target sequence"). It may be labelled with a detectable moiety such as a radioisotope, antigen or chemiluminescent moiety. A background description of the use of nucleic acid hybridization as a procedure for the detection of particular nucleic acid sequences is described by Kohne, U.S. Pat. No. 4,851,330, and Hogan et al., EPO Patent Application No. PCT/US87/03009, entitled "Nucleic Acid Probes for Detection and/Or Quantitation of Non-Viral Organisms."

Hogan et al., supra, also describes methods for determining the presence of RNA-containing organisms in a sample which might contain such organisms. These methods require probes sufficiently complementary to hybridize to the ribosomal RNA (rRNA) of one or more non-viral organisms or groups of non-viral organisms. The mixture is then incubated under specified hybridization conditions, and assayed for hybridization of the probe and any test sample rRNA.

Hogan et al. also describes probes which detect only specifically targeted rRNA subunit subsequences in particular organisms or groups of organisms in a sample, even in the presence of many non-related organisms, or in the presence of the closest known phylogenetic neighbors. Specific examples of hybridization assay probes are provided for *Mycobacterium avium, Mycobacterium intracellulare, Mycobacterium tuberculosis, Mycobacterium africanum, Mycobacterium boris, Mycobacterium microti,* the genus Mycobacterium, *Mycoplasma pneumoniae,* the genus Legionella, *Chlamydia trachomatis,* the genus Campylobacter, Enterococcus, the genus Pseudomonas group I, *Enterobacter cloacae, Proteus mirabilis,* the genus Salmonella, *Escherichia coli,* bacteria, fungi, and *Neisseria gonorrhoeae.* Such probe sequences are said not to cross react with nucleic acids except for the specific species for which the probe is designed, under appropriate hybridization stringency conditions.

SUMMARY OF THE INVENTION

This invention discloses and claims novel probes for the detection of *Coccidioides immitis.* These probes are capable of distinguishing between *Coccidioides immitis* and its known closest phylogenetic neighbors. These probes detect unique rRNA and gene sequences encoding rRNA, and may be used in an assay for the detection and/or quantitation of *Coccidioides immitis,* e.g., in samples of sputum, urine, blood, tissue sections, food, soil and water.

*Coccidioides immitis* is the etiologic agent of the fungal disease coccidioidomycosis (San Joaquin Valley Fever). Infection in man and other animals usually occurs following inhalation of arthroconidia into the lungs. Disease may be evident after an incubation period of one to four weeks. Approximately 60 percent of those infections are asymptomatic or characterized by a self-limiting upper respiratory infection. The remaining 40 percent of infections proceed to the lower respiratory tract resulting in mild or severe pneumonia which may resolve spontaneously or progress to form pulmonary nodules or cavities, occasionally resembling tuberculosis or carcinoma. In rare cases, the infection may disseminate to almost any organ of the body, including the skin, bone and central nervous system.

Conventional laboratory identification methods used to identify *C. immitis* include culture on fungal media, growth rate, colony morphology, microscopic morphology, animal inoculation and biochemical tests. Identification begins with culture of the specimen on fungal media. The time required for growth to a visible, cobweb-like colony varies from 3 to 21 days. The mature colony morphology varies. Additional growth is needed before the characteristic microscopic sporulation pattern of alternating arthroconidia may be seen. Many species of fungi other than *C. immitis* may produce similar colony and sporulation patterns, including such naturally occurring soil fungi as Malbranchea and Uncinocarpus spp. Some yeast-like organisms such as Geotrichum and Trichosporon spp. may also resemble *C. immitis.* Therefore, additional testing is needed to definitively identify this organism.

Animal inoculation is sometimes used to produce the species-specific spherules characteristic of *C. immitis.* Other confirmatory tests based on exoantigen extraction have been described. These tests may take 3 to 5 days or longer to perform.

In contrast, the use of the DNA probes of this invention identifies *C. immitis* isolated from culture in less than an hour.

Thus, in a first aspect, the invention features a hybridization assay probe able to distinguish *Coccidioides immitis* from its known closest phylogenetic neighbors, e.g., other Coccidioides species.

In preferred embodiments, the probe is complementary to rRNA or rDNA, e.g., a variable region of rRNA; at least 50% of the nucleotides in the oligonucleotide probe are able to hybridize to a contiguous series of bases in at least one variable region of ribosomal nucleic acid in *Coccidioides immitis*; the probe is a nucleotide polymer able to hybridize to the rRNA of the species *Coccidioides immitis* corresponding to 23 bases beginning at base 330 of *S. cerevisiae* 28S rRNA, or a nucleotide polymer complementary thereto; and the oligonucleotide comprises, consists essentially of, or consists of the sequence (SEQ ID NO: 1) CAAGGAACT- TATGCCGTGGCTGC or oligonucleotides complementary thereto, with or without a helper probe, as described below.

By "consists essentially of" is meant that the probe is provided as a purified nucleic acid which hybridizes under stringent hybridizing conditions with the desired organism and not with other related organisms. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer able to hybridize to the above oligonucleotides, a nucleic acid hybrid formed with the above oligonucleotides, and a nucleic acid sequence substantially complementary thereto.

The probes of this invention offer a rapid, non-subjective method of identification and quantitation of fungi by detecting the presence of specific rRNA sequences unique to all species and strains of *Coccidioides immitis.*

Other features and advantages of the invention will be apparent from the following description of the preferred embodiments thereof, and from the claims.

DESCRIPTION OF THE PREFERRED EMBODIMENTS

Probes

We have discovered DNA probes complementary to a particular rRNA sequence obtained from *Coccidioides immitis*. Furthermore, we have successfully used those probes in a specific assay for the detection of *Coccidioides immitis*, distinguishing it from its known and presumably most closely related taxonomic or phylogenetic neighbors.

With the exception of viruses, all prokaryotic organisms contain rRNA genes encoding RNA homologous to 5S rRNA, 16S rRNA and a larger rRNA molecule known as 23S rRNA. In the eukaryotes these rRNA molecules are the 5S rRNA, 18S rRNA and 28S rRNA which are substantially similar to the prokaryotic molecules. Using methods known to those skilled in the art, variable regions of rRNA sequences from the 28S rRNA of *Coccidioides immitis* were identified as described below. Other such sequences can be identified using equivalent techniques. These methods include partially or fully sequencing the rRNA of *Coccidioides immitis* and closely related phylogenetic neighbors, aligning the sequences to reveal areas of maximum homology, and examining the alignment for regions with sequence variation. The examples provided below are thus not limiting in this invention.

With respect to sequencing, complementary oligonucleotide primers of about 10–100 bases in length were hybridized to conserved regions in purified rRNA that are specific to the 5S, 16S, or 23S subunits and extended with the enzyme reverse transcriptase. Chemical degradation or dideoxynucleotide-terminated sequencing reactions were used to determine the nucleotide sequence of the extended product. Lane et al., 82 *Proc. Nat'l Acad. Sci. USA,* 6955, 1985. In a less preferred method, genomic ribosomal RNA sequences may also be determined by standard procedure.

It is not always necessary to determine the entire nucleic acid sequence in order to obtain a probe sequence. Extension from any single oligonucleotide primer can yield up to 300–400 bases of sequence. When a single primer is used to partially sequence the rRNA of the target organism and organisms closely related to the target, an alignment can be made as outlined below. If a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Once sequences are aligned it is possible to find the regions in which the primary sequence is variable.

We have identified variable regions by comparative analysis of rRNA sequences both published in the literature and sequences which we have determined. Computers and computer programs which may be used or adapted for the purposes herein disclosed are commercially available. Since the sequence evolution at each of the variable regions (for example, spanning a minimum of 10 nucleotides) is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and %G and %C result in a Tm about 2°–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form (i.e., those having at least about 14 out of 17 bases in a contiguous series of bases being complementary); hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes, the differences in these Tm values should be as large as possible (e.g,., at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intramolecular hybrids. By designing a probe so that a substantial portion of the sequence of interest is single stranded, the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone et al., 12 *Nucleic Acids Research* 4051, 1984. Other well-known methods for construction of synthetic oligonucleotides may, of course, be employed. 2 J. Sambrook, E. F. Fritsch and T. Maniatis, *Molecular Cloning* 11 (2d ed. 1989).

Once synthesized, selected oligonucleotide probes may also be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. Isotopic labels include $^{3}H$, $^{35}S$, $^{32}P$, $^{125}I$, Cobalt and $^{14}C$. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting. The detection method selected will depend upon the hybridization conditions and the particular radio-isotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. 2 J. Sambrook, E. F. Fritsch and T. Maniatis, *Molecular Cloning,* 11.51 (2d ed. 1989). Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., Patent Application Serial No. 613,603 filed Nov. 8, 1990, entitled "Homogeneous Protection Assay," hereby incorporated by reference herein.

For Tm measurement using a Hybridization Protection Assay (HPA) the following technique is used. A probe:target hybrid is formed in target excess in a lithium succinate buffered solution containing lithium lauryl sulfate. Aliquots of this hybrid are diluted in the hybridization buffer and incubated for five minutes at various temperatures starting below that of the anticipated Tm (typically 55° C.) and increasing in 2–5 degree increments. This solution is then diluted with a mildly alkaline borate buffer and incubated at a lower temperature (for example 50° C.) for ten minutes. Under these conditions the acridinium ester attached to a single stranded probe is hydrolyzed while that attached to hybridized probe is relatively protected from hydrolysis. The amount of chemiluminescence remaining is proportional to the amount of hybrid, and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which effect relative hybrid stability during thermal denaturation. 2 J. Sambrook, E. F. Fritsch and T. Maniatis, *Molecular Cloning,* 9.51 (2d ed. 1989).

Rate of hybridization may be measured by determining the $C_0T_{1/2}$. The rate at which a probe hybridizes to its target is a measure of the thermal stability of the target secondary structure in the probe region. The standard measurement of hybridization rate is the $C_0T_{1/2}$ which is measured as moles of nucleotide per liter times seconds. Thus, it is the concentration of probe times the half-life of hybridization at that concentration. This value is determined by hybridizing various amounts of probe to a constant amount of hybrid for a fixed time. For example, 0.05 pmol of target is incubated with 0.0012, 0.025, 0.05, 0.1 and 0.2 pmol of probe for 30 minutes. The amount of hybrid after 30 minutes is measured by HPA as described above. The signal is then plotted as a log of the percent of maximum Relative Light Units (RLU) (from the highest probe concentration) versus probe concentration (moles of nucleotide per liter). RLU are a measurement of the quantity of photons emitted by the labelled-probe measured by the luminometer. The $C_0T_{1/2}$ is found graphically from the concentration corresponding to 50% of maximum hybridization multiplied by the hybridization time in seconds. These values range from $9.0\times10^{-6}$ to $9\times10^{-5}$ with the preferred values being less than $3.5\times10^{-5}$.

As described by Kohne and Kacian (U.S. Ser. No. 816, 711, entitled "Accelerated Nucleic Acid Reassociation Method, "filed Jan. 7, 1986 abandoned in favor of U.S. application Ser. No. 644,879, filed Jan. 23, 1991, hereby incorporated by reference herein) other methods of nucleic acid reassociation can be used.

The following example sets forth a synthetic probe complementary to a unique rRNA sequence, or the corresponding gene, from a target organism, *Coccidioides immitis,* and its use in a hybridization assay.

EXAMPLE

A probe specific for *C. immitis* was identified by sequencing with a primer complementary to the 28S rRNA. The following sequence was characterized and shown to be specific for *Coccidioides immitis*; (SEQ ID NO: 1) CAAGGAACTTATGCCGTGGCTGC. Several phylogenetically near neighbors including *Blastomyces dermatitidis, Candida albicans, Candida tropicalis, Saccharomyces cerevisiae, Saccharomyces carlsbergensis, Histoplasma capsulatum,* and *Cryptococcus neoformans* were used as comparisons with the sequence of *C. immitis.*

To demonstrate the reactivity and specificity of the probe for *C. immitis*, it was used in a hybridization assay. The probe was first synthesized with a non-nucleotide linker, then labelled with a chemiluminescent acridinium ester as described in EPO Patent Application No. PCT/US88/03361, entitled "Acridinium Ester Labeling and Purification of Nucleotide Probes filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled-probe measured by the luminometer. The conditions of hybridization, hydrolysis and detection are described in Arnold, et al., 35 Clin. Chem. 1588, 1989.

Nucleic acid hybridization was enhanced by the use of "Helper Probes" as disclosed in Hogan et al., U.S. Pat. No. 5,030,557, entitled "Means and Methods for Enhancing Nucleic Acid Hybridization", hereby incorporated by reference herein. RNA was hybridized to the acridinium ester-labeled probe in the presence of unlabeled Helper probes. The probe corresponded to oligonucleotide SEQ ID NO: 1 with helpers: (SEQ ID NO:2) GCTCCGCATGGAGCCAGATTTCAAATTTGAGCTTTTGCCG, (SEQ ID NO: 3) CGAAGTGTCCTCTCCAAATTACAACTCG, (SEQ ID NO:4) GGATTCTCACCCTCTATGACGTCCTGTT, and (SEQ ID NO: 5) CGAAGGAACTTCGCATAGGCCGGTCCAGCAGCCAGAGACG. The Tm to *C. immitis* RNA was 69.4° C. under the conditions of the assay described above.

In the following experiment, RNA released from one colony or >$10^8$ organisms was assayed. An example of such a method is provided by Murphy et al., U.S. Ser. No. 841,860, entitled "Method for Releasing RNA and DNA from Cells", filed Mar. 20, 1986, abandoned in favor of U.S. Ser. No. 298,765, filed Jan. 17, 1989, hereby incorporated by reference herein. An RLU value greater than 50,000 RLU is a positive reaction; less than 50,000 is a negative reaction.

The following data show that the probes did not cross react with organisms from a wide phylogenetic cross section. The samples were also tested with a probe which has a very broad specificity. A positive signal from this probe provided confirmation of sample adequacy.

PHYLOGENETIC CROSS SECTION AND CLOSELY RELATED ORGANISMS

| NAME | ATCC # | RLU |
|---|---|---|
| *Acremonium strictum* | 10141 | 8499 |
| *Arachniotus flavoluteus* | 28364 | 5621 |
| *Arthroderma tuberculatum* | 26700 | 7850 |
| *Aspergillus flavus* | 10124 | 9339 |
| *Aspergillus nidulans* | 10074 | 5497 |
| *Aureobasidium pullulans* | 16622 | 2957 |
| *Auxarthron thaxteri* | 15598 | 4827 |
| *Blastomyces dermatitidis* | 26199 | 6813 |
| *Blastoschizomyces capitatus* | 28576 | 2997 |
| *Candida albicans* | 18804 | 2906 |
| *Candida glabrata* | 48435 | 1563 |
| *Candida krusei* | 6258 | 1741 |
| *Candida parapsilosis* | 22019 | 2177 |
| *Candida tropicalis* | 13803 | 4291 |
| *Chaetonium globosum* | 44699 | 3561 |
| *Chionosphaera apobasidialis* | 52639 | 4713 |
| *Chrysosporium keratinophilum* | 14803 | 7342 |
| *Cladosporium herbarum* | 28987 | 1915 |
| *Coccidioides immitis* | 28868 | 494252 |
| *Coccidioides immitis* | 46900 | 636924 |
| *Coccidioides immitis* | 38146 | 701760 |
| *Coccidioides immitis* | 34615 | 682511 |

-continued

| PHYLOGENETIC CROSS SECTION AND CLOSELY RELATED ORGANISMS | | |
|---|---|---|
| NAME | ATCC # | RLU |
| *Coccidioides immitis* | 38149 | 644880 |
| *Coccidioides immitis* | 34616 | 695645 |
| *Corynascus sepedonium* | 42828 | 3523 |
| *Cryptococcus albidus* var. *albidus* | 10666 | 2383 |
| *Cryptococcus albidus* var. *diffluens* | 34141 | 1949 |
| *Cryptococcus laurentii* | 18803 | 7752 |
| *Cryptococcus luteolus* | 32044 | 3187 |
| *Cryptococcus neoformans* | 32045 | 4582 |
| *Cryptococcus terreus* | 11799 | 4978 |
| *Cryptococcus uniguttulatus* | 34143 | 2337 |
| *Epidermophyton floccosum* | 50266 | 5169 |
| *Filobasidium capsuligenum* | 22179 | 6677 |
| *Fusarium oxysporum* | 48112 | 3394 |
| *Geomyces asperulatus* | 34521 | 5718 |
| *Geotricum candidum* | 34614 | 2881 |
| *Gymnoascus dugwayensis* | 18899 | 5037 |
| *Histoplasma capsulatum* | 11407 | 2406 |
| *Malbranchea absoluta* | 34522 | 7479 |
| *Microsporum gypseum* | 24102 | 2787 |
| *Myxotricum deflexum* | 15686 | 5365 |

-continued

| PHYLOGENETIC CROSS SECTION AND CLOSELY RELATED ORGANISMS | | |
|---|---|---|
| NAME | ATCC # | RLU |
| *oidiodendron echinulatum* | 16287 | 3084 |
| *Paracoccidioides brasiliensis* | 60855 | 3116 |
| *Penicillium notatum* | 11625 | 5191 |
| *Prototheca wickerhamii* | 16529 | 3960 |
| *Pseudallescheria boydii* | 58034 | 1557 |
| *Renispora flavissima* | 38503 | 2416 |
| *Rhizopus oligosporus* | 22959 | 3941 |
| *Rhodotorula glutinis* | 32765 | 1747 |
| *Saccharomyces cerevisiae* | 18824 | 3465 |
| *Scopulariopsis acremonium* | 58636 | 5429 |
| *Sporothrix schenckii* | 14284 | 3070 |
| *Trichophyton mentagrophytes* | 18748 | 3296 |
| *Trichosporon beigelii* | 28592 | 4750 |
| *Uncinocarpus reesii* | 34533 | 1402 |

The above data confirm that the novel probes herein disclosed and claimed are capable of distinguishing *Coccidioides immitis* from its known nearest phylogenetic neighbors.

Other embodiments are within the following claims.

I claim:

1. A hybridization assay probe targeted to *Coccidioides immitis* 28S rRNA or rDNA encoding said 28S rRNA, comprising an oligonucleotide able to distinguish *Coccidioides immitis* from *Blastomyces dermatitidis, Candida albicans, Candida tropicalis, Saccharomyces cerevisiae, Saccharomyces carlsbergensis, Histoplasma capsulatum,* and *Cryptococcus neoformans.*

2. The probe of claim 1, wherein said probe is 10 to 100 bases in length and has at least 82% perfect complementarity to a region at least 10 bases in length present in a sequence selected from the group consisting of:
SEQ ID NO: 1: CAAGGAACTT ATGCCGTGGC TGC,
SEQ ID NO: 6: GCAGCCACGG CATAAGTTCC TTG, and
SEQ ID NO: 7: GCAGCCACGG CAUAAGUUCC UUG.

3. The probe of claim 1, wherein said probe is 15 to 100 bases in length and has at least 14 out of 17 contiguous bases perfectly complementary to a target sequence present in a nucleic acid sequence selected from the group consisting of:
SEQ ID NO: 1: CAAGGAACTT ATGCCGTGGC TGC,
SEQ ID NO: 6: GCAGCCACGG CATAAGTTCC TTG, and
SEQ ID NO: 7: GCAGCCACGG CAUAAGUUCC UUG.

4. The probe of claim 3, wherein said probe is 20 to 50 bases in length.

5. The probe of claim 3, wherein said probe has a nucleotide base sequence selected from the group consisting of:
SEQ ID NO: 1: CAAGGAACTT ATGCCGTGGC TGC,
SEQ ID NO: 6: GCAGCCACGG CATAAGTTCC TTG, SEQ ID NO: 7: GCAGCCACGG CAUAAGUUCC JUG, and

SEQ ID NO: 8: CAAGGAACUU AUGCCGUGGC UGC.

6. The probe of claim 5, wherein said probe is 23 to 50 bases in length.

7. The probe of claim 5, wherein said probe consists of said nucleotide base sequence.

8. The probe of claim 7, wherein said probe contains a detectable label selected from the group consisting of: radioisotope fluorescent molecule, chemiluminescent molecule, enzyme, cofactor, enzyme substrate, and hapten.

9. The probe of claim 8, wherein said detectable label is an acridinium ester.

10. A probe mix comprising:

a) a hybridization assay probe targeted to *Coccidioides immitis* 28S rRNA or rDNA encoding said 28S rRNA, comprising an oligonucleotide able to distinguish *Coccidioides immitis* from *Blastomyces dermatitidis, Candida albicans, Candida tropicalis, Saccharomyces cerevisiae, Saccharomyces carlsbergensis, Histoplasma capsulatum,* and *Cryptococcus neoformans;* and b) at least one helper probe oligonucleotide having a helper probe nucleotide sequence selected from the group consisting of:

SEQ ID NO: 2: GCTCCGCATG GAGCCAGATT TCAAATTTGA GCTTTTGCCG,

SEQ ID NO: 3: CGAAGTGTCC TCTCCAAATT ACAACTCG,

SEQ ID NO: GGATTCTCAC CCTCTATGAC GTCCTGTT, and

SEQ ID NO: 5: CGAAGGAACT TCGCATAGGC CGGTCCAGCA GCCAGAGACG.

11. The probe mix of claim 10, wherein said hybridization assay probe is 10 to 100 bases in length and has at least 82% perfect complementarity to a region at least 10 bases in length present in a sequence selected from the group consisting of:

SEQ ID NO: 1: CAAGGAACTT ATGCCGTGGC TGC,

SEQ ID NO: 6: GCAGCCACGG CATAAGTTCC TTG, and

SEQ ID NO: 7: GCAGCCACGG CAUAAGUUCC UUG.

12. The probe mix of claim 10, wherein said hybridization assay probe is 15 to 100 bases in length and has at least 14 out of 17 contiguous bases perfectly complementary to a target sequence present in a nucleic acid sequence selected from the group consisting of:

SEQ ID NO: 1: CAAGGAACTT ATGCCGTGGC TGC,

SEQ ID NO: 6: GCAGCCACGG CATAAGTTCC TTG, and

SEQ ID NO: 7: GCAGCCACGG CAUAAGUUCC UUG.

13. The probe mix of claim 12, wherein said hybridization assay probe is 20 to 50 bases in length.

14. The probe mix of claim 13, wherein said hybridization assay probe has a sequence selected from the group consisting of:

SEQ ID NO: 1: CAAGGAACTT ATGCCGTGGC TGC,

SEQ ID NO: 6: GCAGCCACGG CATAAGTTCC TTG,

SEQ ID NO: 7: GCAGCCACGG CAUAAGUUCC UUG, and

SEQ ID NO: 8: CAAGGAACUU AUGCCGUGGC UGC.

15. The probe mix of claim 14, wherein said hybridization assay probe consists of said probe nucleotide sequence, and said at least one helper probe consists of said helper probe nucleotide sequence.

16. The probe mix of claim 15, wherein said at least one helper probe consists of a first helper probe of SEQ ID NO: 2: GCTCCGCATG GAGCCAGATT TCAAATTTGA GCTTTTGCCG, a second helper probe of SEQ ID NO: 3: CGAAGTGTCC TCTCCAAATT ACAACTCG, a third helper probe of SEQ ID NO: 4: GGATTCTCAC CCTCTATGAC GTCCTGTT, or a fourth helper probe of SEQ ID NO: 5: CGAAGGAACT TCGCATAGGC CGGTCCAGCA GCCAGAGACG.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 23
( B ) TYPE: nucleic acid
( C ) STRANDEDNESS: single
( D ) TOPOLOGY: linear ( i i ) SEQUENCE DESCRIPTION: SEQ ID NO: 1:

CAAGGAACTT ATGCCGTGGC TGC 23

( 2 ) INFORMATION FOR SEQ ID NO: 2:

( i ) SEQUENCE CHARACTERISTICS:
( A ) LENGTH: 40
( B ) TYPE: nucleic acid
( C ) STRANDEDNESS: single
( D ) TOPOLOGY: linear ( i i ) SEQUENCE DESCRIPTION: SEQ ID NO: 2:

GCTCCGCATG GAGCCAGATT TCAAATTTGA GCTTTTGCCG 40

( 2 ) INFORMATION FOR SEQ ID NO: 3:

( i ) SEQUENCE CHARACTERISTICS:
( A ) LENGTH: 28
( B ) TYPE: nucleic acid
( C ) STRANDEDNESS: single
( D ) TOPOLOGY: linear ( i i ) SEQUENCE DESCRIPTION: SEQ ID NO: 3:

CGAAGTGTCC TCTCCAAATT ACAACTCG 28

( 2 ) INFORMATION FOR SEQ ID NO: 4:

-continued ( i ) SEQUENCE CHARACTERISTICS:
( A ) LENGTH: 28
( B ) TYPE: nucleic acid
( C ) STRANDEDNESS: single
( D ) TOPOLOGY: linear ( i i ) SEQUENCE DESCRIPTION: SEQ ID NO: 4:

GGATTCTCAC CCTCTATGAC GTCCTGTT 28

( 2 ) INFORMATION FOR SEQ ID NO: 5:

( i ) SEQUENCE CHARACTERISTICS:
( A ) LENGTH: 40
( B ) TYPE: nucleic acid
( C ) STRANDEDNESS: single
( D ) TOPOLOGY: linear ( i i ) SEQUENCE DESCRIPTION: SEQ ID NO: 5:

CGAAGGAACT TCGCATAGGC CGGTCCAGCA GCCAGAGACG 40

( 2 ) INFORMATION FOR SEQ ID NO: 6:

( i ) SEQUENCE CHARACTERISTICS:
( A ) LENGTH: 23
( B ) TYPE: nucleic acid
( C ) STRANDEDNESS: single
( D ) TOPOLOGY: linear ( v i i ) SEQUENCE DESCRIPTION: SEQ ID NO: 6:

GCAGCCACGG CATAAGTTCC TTG 23

( 2 ) INFORMATION FOR SEQ ID NO: 7:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO: 7:

GCAGCCACGG CAUAAGUUCC UUG 23

( 2 ) INFORMATION FOR SEQ ID NO: 8:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO: 8:

CAAGGAACUU AUGCCGUGGC UGC 23